(12) United States Patent
Cho et al.

(10) Patent No.: US 7,473,700 B2
(45) Date of Patent: Jan. 6, 2009

(54) 1,2,4-TRIAZOLE DERIVATIVES, PROCESSES FOR THE PREPARATION THEREOF, AND PHARMACEUTICAL COMPOSITIONS CONTAINING THE SAME

(75) Inventors: Il Hwan Cho, Seoul (KR); Dong Hyun Ko, Gwacheon (KR); Myeong Yun Chae, Sungnam (KR); In Ki Min, Yongin (KR); Young Hoon Kim, Seoul (KR); Kyu Jeong Yeon, Yongin (KR); Jong Hoon Kim, Anyang (KR); Sung Hak Jung, Seoul (KR); Sang Wook Park, Suwon (KR); Il Hwan Kim, Daejeon (KR); Hyung Chul Ryu, Yongin (KR); Ji Young Noh, Busan (KR); Hyun Jung Park, Jeonju (KR); Jie Eun Park, Wonju (KR); Young Mee Chung, Suwon (KR)

(73) Assignee: CJ Corporation, Seoul (KR)

( * ) Notice: Subject to any disclaimer, the term of this patent is extended or adjusted under 35 U.S.C. 154(b) by 461 days.

(21) Appl. No.: 10/536,408

(22) PCT Filed: Nov. 26, 2003

(86) PCT No.: PCT/KR03/02574

§ 371 (c)(1),
(2), (4) Date: May 26, 2005

(87) PCT Pub. No.: WO2004/048347

PCT Pub. Date: Jun. 10, 2004

(65) Prior Publication Data

US 2006/0074118 A1    Apr. 6, 2006

(30) Foreign Application Priority Data

Nov. 27, 2002    (KR) .................. 10-2002-0074348

(51) Int. Cl.
*A61K 31/41* (2006.01)
*C07D 249/08* (2006.01)

(52) U.S. Cl. .................... 514/383; 548/262.2

(58) Field of Classification Search ............. 514/383; 548/262.2

See application file for complete search history.

(56) References Cited

U.S. PATENT DOCUMENTS

| 5,466,823 | A | 11/1995 | Talley et al. |
| 5,633,272 | A | 5/1997 | Talley et al. |
| 6,849,652 | B1 * | 2/2005 | Cho et al. .................. 514/383 |
| 7,019,144 | B2 * | 3/2006 | Cho et al. ............... 546/272.4 |
| 7,135,572 | B2 * | 11/2006 | Cho et al. ............... 546/272.4 |
| 7,169,929 | B2 * | 1/2007 | Cho et al. ............... 546/269.4 |
| 7,230,010 | B2 * | 6/2007 | Cho et al. .................. 514/311 |
| 2003/0125368 | A1 | 7/2003 | Sakya et al. |

FOREIGN PATENT DOCUMENTS

| EP | 0 176 444 A1 | 4/1986 |
| JP | 56-049371 | 5/1981 |
| JP | 59-039880 | 3/1984 |
| JP | 08-092225 | 4/1996 |
| WO | WO 95/00501 | 1/1995 |
| WO | WO 03/040110 A1 | 5/2003 |

OTHER PUBLICATIONS

Battistini B., et al., "Cox-1 and Cox-2:Toward the Development of More Selective NSAIDs", DN&P, Oct. 1994, pp. 501-512, vol. 7(8).
Hüll M., et al., "Anti-inflammatory drugs: a hope for Alzheimer's disease?", Exp. Opin. Invest. Drugs, 2000, pp. 671-683, vol. 9(4).
Kirschenbaum A., et al., "The Role of Cyclooxygenase-2 in Prostate Cancer", Urology, Aug. 2001, pp. 127-131, vol. 58(Supplemental 2A).
Reitz D., et al., "Selective Cyclooxygenase Inhibitors", Annual Report in Medicinal Chemistry, 1995, pp. 179-188, vol. 30.
Szilágyi G., et al., "Preparation and antiarthritic activity of new 1,5-diaryl-3-alkylthio-1H-1,2,4-triazoles and corresponding sulfoxides and sulfones", Eur. J. Med. Chem., 1990, pp. 95-101, vol. 25, XP002346280.
Van Cutsem E., et al., "Recent advances in the management of colorectal cancer", European Journal of Cancer, 2001, pp. 2302-2309, vol. 37.
Vane J., "Towards a better aspirin", Nature, Jan. 1994, pp. 215-216, vol. 367.

* cited by examiner

*Primary Examiner*—Rei-Tsang Shiao
*Assistant Examiner*—Susannah Chung
(74) *Attorney, Agent, or Firm*—Rothwell, Figg, Ernst & Manbeck, P.C.

(57) ABSTRACT

A 1,2,4-triazole derivative of formula 1 or a non-toxic salt thereof, a preparation method thereof, and a pharmaceutical composition containing the derivative or the salt as an active ingredient are provided.

3 Claims, No Drawings

1,2,4-TRIAZOLE DERIVATIVES, PROCESSES FOR THE PREPARATION THEREOF, AND PHARMACEUTICAL COMPOSITIONS CONTAINING THE SAME

CROSS REFERENCE TO RELATED APPLICATION

This application is a 35 U.S.C. § 371 National Phase Entry Application from PCT/KR03/02574, filed Nov. 26, 2003, and designating the U.S.

BACKGROUND OF THE INVENTION

1. Field of the Invention

The present invention relates to a 1,2,4-triazole derivative or a non-toxic salt thereof, a method for preparing the same, and a pharmaceutical composition containing the same as an active ingredient.

2. Description of the Related Art

Most nonsteroidal anti-inflammatory agents are responsible for blocking enzyme, cyclooxygenase (COX) or prostaglandin G/H synthase, to reduce inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that can be easily induced by mitogen, endotoxin, hormone, growth factor, or cytokine.

Prostaglandin is a potent mediator for various pathological and physiological processes. The COX-1 plays important physiological roles such as in the release of endogenous prostaglandin, the maintenance of the shape and the function of stomach, and the blood circulation in the kidney. On the other hand, the COX-2 is induced by an inflammatory factor, hormone, a growth factor, or cytokine. Therefore, the COX-2 is involved in pathological processes of prostaglandin, unlike the constitutive COX-1. In this regard, selective inhibitors of the COX-2 produce fewer and less side effects in terms of action mechanism in comparison with conventional nonsteroidal anti-inflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, they help in preventing premature birth, menstrual irregularity, asthma, and eosinophilic disease.

In addition, it is anticipated that selective inhibitors of the COX-2 would be effective in treating osteoporosis and glaucoma. Utility of selective inhibitors of the COX-2 is well described in publications [John Vane, "Towards a Better Aspirin" in *Nature*, Vol. 367, pp215-216, 1994; Bruno Battistini, Regina Botting and Y. S. Bakhle, "COX-1 and COX-2: Toward the Development of More Selective NSAIDs" in *Drug News and Perspectives*, Vol. 7, pp501-512, 1994; Urology, Vol. 58, pp127, 2001; David B. Reitz and Karen Seibert, "Selective Cyclooxygenase Inhibitors" in *Annual Reports in Medicinal Chemistry*, James A. Bristol, Editor, Vol. 30, pp179-188, 1995].

Various selective COX-2 inhibitors having different structures are known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings.

One selective COX-2 inhibitor, Celecoxib of formula 70 is disclosed in U.S. Pat. No. 5,466,823. The Celecoxib is a substituted pyrazolyl benzenesulfonamide derivative.

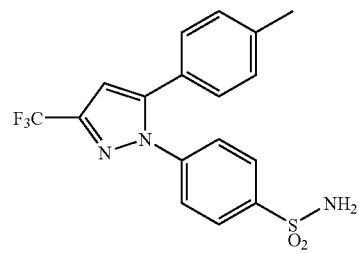

Formula 70

Another selective COX-2 inhibitor, Rofecoxib of formula 71 is disclosed in WO 95/00501. The Rofecoxib has a diary heterocyclic structure with a central furanone ring.

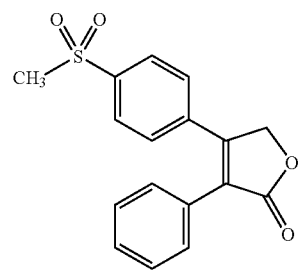

Formula 71

Valdecoxib of formula 72 as another selective COX-2 inhibitor is disclosed in U.S. Pat. No. 5,633,272. The Valdecoxib has a phenylsulfonamide moiety with a central isoxazole ring.

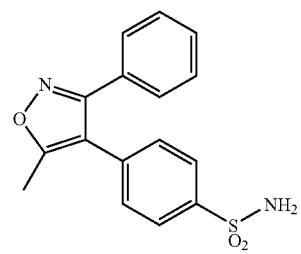

Formula 72

The selective COX-2 inhibitors of formulas 70 to 72 are effective inflammatory therapeutic agents with fewer and less side effects in comparison with conventional nonsteroidal anti-inflammatory agents.

SUMMARY OF THE INVENTION

An aspect of the present invention provides a 1,2.4-triazole derivative of formula 1 or a non-toxic salt thereof.

Another aspect of the present invention provides a method for preparing a 1,2.4-triazole derivative or a non-toxic salt thereof.

Another aspect of the present invention provides a pharmaceutical composition comprising a 1,2.4-triazole derivative or a non-toxic salt thereof as an active ingredient for the treatment of fever, pain, and inflammation.

DETAILED DESCRIPTION OF THE INVENTION

According to an aspect of the present invention, there is provided a 1,2.4-triazole derivative represented by formula 1:

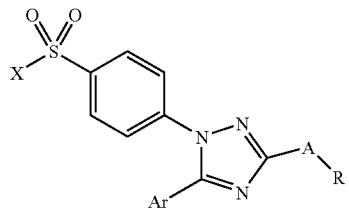

Formula 1 wherein:
X represents methyl or amino;
Ar represents phenyl or phenyl substituted with one or more radicals selected from $C_1$-$C_6$ alkoxy and halogen;
A represents O or S; and
R represents H, $C_1$-$C_6$ alkyl, trifluoro $C_1$-$C_6$ alkyl, $C_3$-$C_6$ cycloalkyl, $C_1$-$C_6$ alkyl substituted with cyano or halogen, propagyl, allyl, or benzyl;
or a non-toxic salt thereof.

The 1,2,4-triazole derivative of formula 1 may be present in a form of a non-toxic salt. The term, "non-toxic salt" as used herein refers to a pharmaceutically acceptable toxin-free salt, including an organic salt and an inorganic salt.

The 1,2,4-triazole derivative of formula 1 may be present in a form of an organic acid salt or an inorganic acid salt.

Examples of the organic acid salt or the inorganic acid salt of the 1,2,4-triazole derivative of formula 1 include, but are not limited to, a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, icethionic acid, lactic acid, maleic acid, malic acid, madelic acid, methane sulfonic acid, mucinic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. Preferably, a salt of succinic acid, hydrobromic acid, hydrochloric acid, maleic acid, methanesulfonic acid, phosphoric acid, sulfuric acid, or tartaric acid is used.

The 1,2,4-triazole derivative of the present invention preferably includes:
4-(3-mercapto-5-phenyl-1,2,4-triazole-1-yl)-benzenesulfonamide;
4-(3-hydroxy-5-phenyl-1,2,4-triazole-1-yl)-benzenesulfonamide;
4-[3-hydroxy-5-(4-methoxyphenyl)-1,2,4-triazole-1-yl]-benzenesulfonamide;
4-[3-hydroxy-5-(4-ethoxyphenyl)-1,2,4-triazole-1-yl]-benzenesulfonamide;
4-[3-hydroxy-5-(4-fluorophenyl)-1,2,4-triazole-1-yl]-benzenesulfonamide;
4-[3-hydroxy-5-(4-bromophenyl)-1,2,4-triazole-1-yl]-benzenesulfonamide;
4-[3-hydroxy-5-(3-fluoro-4-methoxyphenyl)-1,2,4-triazole-1-yl]-benzenesulfonamide;
1-(4-methanesulfonylphenyl)-5-phenyl-1H-1,2,4-triazole-3-ol;
1-(4-methanesulfonylphenyl)-5-(4-methoxyphenyl)-1H-1,2,4-triazole-3-ol;
4-(3-methoxy-5-phenyl-1,2,4-triazole-1-yl)-benzenesulfonamide;
4-[3-methoxy-5-(4-fluorophenyl)-1,2,4-triazole-1-yl]-benzenesulfonamide;
4-[3-methoxy-5-(4-methoxyphenyl)-1,2,4-triazole-1-yl]-benzenesulfonamide;
4-[3-methoxy-5-(4-bromophenyl)-1,2,4-triazole-1-yl]-benzenesulfonamide;
4-[3-methoxy-5-(3-fluoro-4-methoxyphenyl)-1,2,4-triazole-1-yl]-benzenesulfonamide;
4-(3-methylthio-5-phenyl-1,2,4-triazole-1-yl)-benzenesulfonamide;
4-(3-ethoxy-5-phenyl-1,2,4-triazole-1-yl)-benzenesulfonamide;
4-[3-ethoxy-5-(4-fluorophenyl)-1,2,4-triazole-1-yl]-benzenesulfonamide;
4-[3-ethoxy-5-(4-methoxyphenyl)-1,2,4-triazole-1-yl]-benzenesulfonamide;
4-[3-ethoxy-5-(3-fluoro-4-methoxyphenyl)-1,2,4-triazole-1-yl]-benzenesulfonamide;
4-(3-ethylthio-5-phenyl-1,2,4-triazole-1-yl)-benzenesulfonamide;
4-[3-propoxy-5-(4-methoxyphenyl)-1,2,4-triazole-1-yl]-benzenesulfonamide;
4-[3-propoxy-5-(4-fluorophenyl)-1,2,4-triazole-1-yl]-benzenesulfonamide;
4-[3-cyclopentyloxy-5-(4-fluorophenyl)-1,2,4-triazole-1-yl]-benzenesulfonamide;
4-[3-cyclopentyloxy-5-(4-methoxyphenyl)-1,2,4-triazole-1-yl]-benzenesulfonamide;
4-[3-cyclohexyloxy-5-(4-fluorophenyl)-1,2,4-triazole-1-yl]-benzenesulfonamide;
4-[3-cyclohexyloxy-5-(4-methoxyphenyl)-1,2,4-triazole-1-yl]-benzenesulfonamide;
4-(3-isopropoxy-5-phenyl-1,2,4-triazole-1-yl)-benzenesulfonamide;
4-[3-isopropoxy-5-(4-fluorophenyl)-1,2,4-triazole-1-yl]-benzenesulfonamide;
4-[3-isopropoxy-5-(-4-methoxyphenyl)-1,2,4-triazole-1-yl]-benzenesulfonamide;
4-(3-isopropylthio-5-phenyl-1,2,4-triazole-1-yl)-benzenesulfonamide;
4-(3-allyloxy-5-phenyl-1,2,4-triazole-1-yl)-benzenesulfonamide;
4-[3-allyloxy-5-(4-fluorophenyl)-1,2,4-triazole-1-yl]-benzenesulfonamide;
4-[3-allyloxy-5-(4-methoxyphenyl)-1,2,4-triazole-1-yl]-benzenesulfonamide;
4-[3-cyanomethoxy-5-(4-fluorophenyl)-1,2,4-triazole-1-yl]-benzenesulfonamide;
4-[3-cyanomethoxy-5-(4-methoxyphenyl)-1,2,4-triazole-1-yl]-benzenesulfonamide;
4-(3-benzyloxy-5-phenyl-1,2,4-triazole-1-yl)-benzenesulfonamide;
4-[3-benzyloxy-5-(3-fluoro-4-methoxyphenyl)-1,2,4-triazole-1-yl]-benzenesulfonamide;
4-[3-(2-chloroethoxy)-5-phenyl-1,2,4-triazole-1-yl]-benzenesulfonamide;
4-[3-(2,2,2-trifluoroethoxy)-5-(4-methoxyphenyl)-1,2,4-triazole-1-yl]-benzenesulfonamide;
4-[3-(2,2,2,-trifluoroethoxy)-5-(4-fluorophenyl)-1,2,4-triazole-1-yl]-benzenesulfonamide;

4-[3-cyclopropoxy-5-phenyl-1,2,4-triazole-1-yl]-benzenesulfonamide;

4-[3-prop-2-ynyloxy-5-(4-methoxyphenyl)-1,2,4-triazole-1-yl]-benzenesulfonamide;

4-[3-prop-2-ynyloxy-5-(4-fluorophenyl)-1,2,4-triazole-1-yl]-benzenesulfonamide;

4-(3-propy-2-nylthio-5-phenyl-1,2,4-triazole-1-yl)-benzenesulfonamide;

1-(4-methanesulfonylphenyl)-3-methoxy-5-phenyl-1H-1,2,4-triazole;

1-(4-methanesulfonylphenyl)-3-methoxy-5-(4-methoxyphenyl)-1H-1,2,4-triazole;

1-(4-methanesulfonylphenyl)-3-ethoxy-5-phenyl-1H-1,2,4-triazole;

1-(4-methanesulfonylphenyl)-3-ethoxy-5-(4-methoxyphenyl)-1H-1,2,4-triazole;

1-(4-methanesulfonylphenyl)-3-isopropoxy-5-phenyl-1H-1,2,4-triazole; and 1-(4-methanesulfonylphenyl)-3-isopropoxy-5-(4-methoxyphenyl)-1H-1,2,4-triazole.

According to another aspect of the present invention, there is provided compound of formula 2 as an intermediate for the synthesis of the 1,2,4-triazole derivative of formula 1:

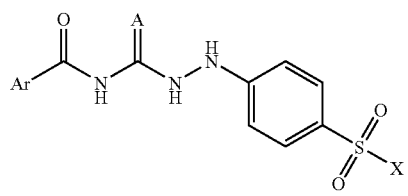

Formula 2 wherein, Ar, A, and X are as defined in formula 1.

According to another aspect of the present invention, there is provided a method for preparing a 1,2,4-triazole derivative of formula 1b, comprising reacting compound of formula 1a with R'—Br or R'—I in the presence of a base:

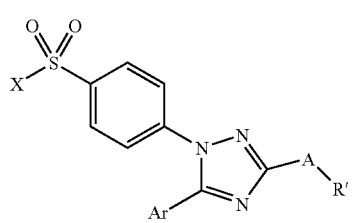

Formula 1b

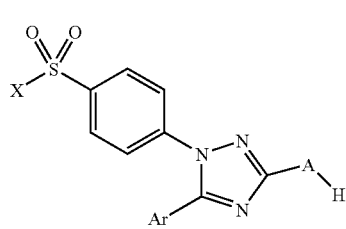

Formula 1a wherein:

X, Ar, and A are as defined in formula 1;

R' represents $C_1$-$C_6$ alkyl, trifluoro $C_1$-$C_6$ alkyl, $C_3$-$C_6$ cycloalkyl, $C_1$-$C_6$ alkyl substituted with cyano or halogen, propagyl, allyl, or benzyl.

The said reaction is preferably carried out in a polar solvent, which includes, but is not limited to DMF, dioxane, DMSO, methylpyrrolidinone, or m-xylene.

The reactions is preferably carried out at 0° C. to 110° C. The reaction time is 5 minutes to 36 hours, depending on the reactants.

The base may be an organic base or an inorganic base. Among the organic base, preferably triethyl amine, trimethyl amine, tripropyl amine, pyridine, or imidazole is used. Among the inorganic base, preferably sodium acetate, sodium hydroxide, sodium hydride, potassium hydroxide, sodium carbonate, or potassium carbonate is used. More preferably, sodium hydride is used.

According to another aspect of the present invention, there is provided a method for preparing a 1,2,4-triazole derivative of formula 1a, comprising refluxing a compound of formula 2 in a basic solvent to form a 1,2,4-triazole:

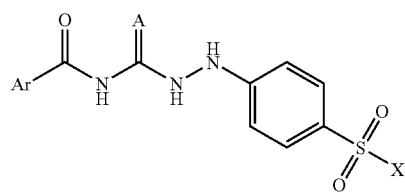

Formula 2 wherein, X, Ar, and A are as defined in formula 1.

The basic solvent is preferably potassium hydroxide, sodium hydroxide, or lithium hydroxide. More preferably, potassium hydroxide is used.

According to another aspect of the present invention, there is provided a method for preparing a compound of formula 2, comprising reacting a compound of formula 3 with a hydrazine derivative of formula 4 in the presence of a base:

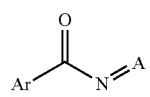

Formula 3

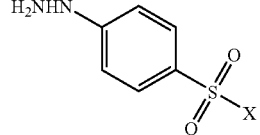

Formula 4 wherein, X, Y, and A are as defined in formula 1.

The said reaction is preferably carried out in a polar solvent, which includes, but is not limited to DMF, dioxane, DMSO, methylpyrrolidinone, or m-xylene.

The reactions is preferably carried out at 0° C. to 110° C. The reaction time is 5 minutes to 36 hours depending on the reactants.

When the reaction is completed, the reaction resultant is extracted with water and an organic solvent such as ethyl acetate, dichloromethane, tetrahydrofuran, or ether, to remove salts. The crude extract is purified by silica gel column chromatography to give the compound of formula 2.

The base to be used herein is an organic base or an inorganic base. Preferably, the organic base is triethyl amine, trimethyl amine, tripropyl amine, pyridine, or imidazole. Preferably, the inorganic base is sodium acetate, sodium hydroxide, sodium hydride, potassium hydroxide, sodium carbonate, or potassium carbonate. More preferably, potassium carbonate is used.

The above compound of formual 3 may be prepared by reacting a benzamide derivative with a oxalyl chloride. The reaction is preferably carried out in a solvent selected from the group consisting of dichloromethane, dichloroethane, and THF. The reactions is preferably carried out at an ambient temperature or by reflux. The reaction time is 1 hour to 24 hours depending on the reactants. When the reaction is completed, the reaction product is preferably obtained by distilling the solvent under reduced pressure without purification processes.

All crude products obtained from the above mentioned reactions are purified via a conventional post-treatment process, for example, chromatography or recrystallization to thereby give final products.

A method for preparing a compound of formula 1 may be expressed in order by the following scheme 1:

of formula 1 or a non-toxic salt thereof as an active ingredient and a pharmaceutically acceptable carrier for treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an anti-inflammatory agent, with reduced side effects.

Conventional nonsteroidal anti-inflammatory agents non-selectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and anti-inflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal anti-inflammatory agents. In particular, due to the reduction of the side effects of conventional nonsteroidal antipyretics, analgesics, and anti-inflammatory agents, the pharmaceutical composi-

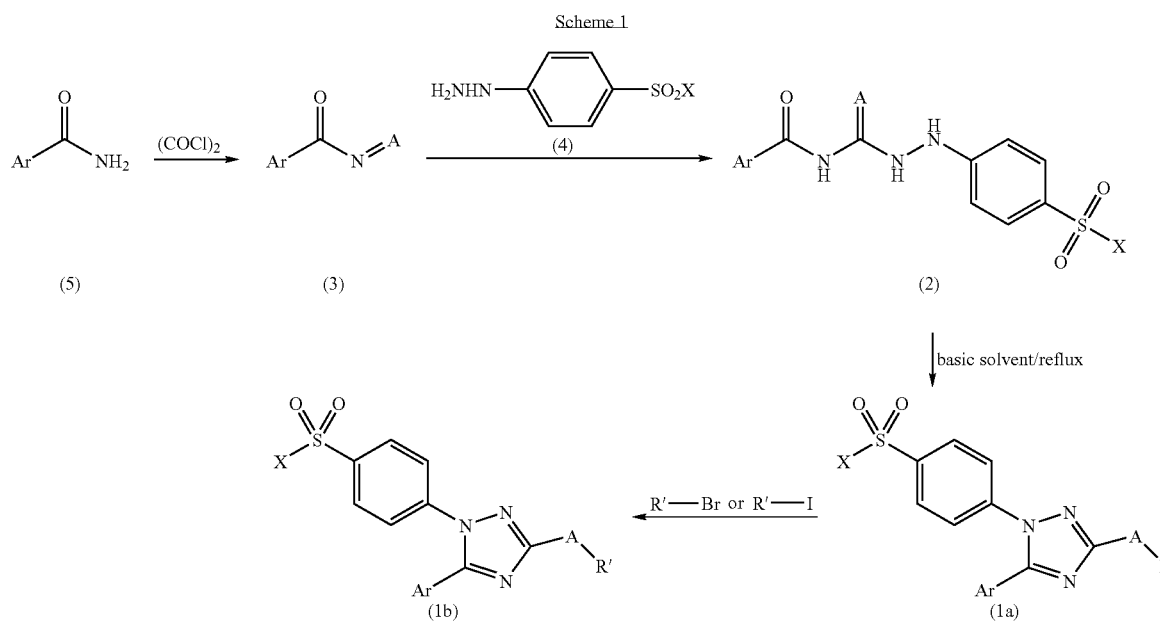

Scheme 1 wherein, X, Y, A, and B are as defined in the above. A hydrazine derivative to be used in the scheme 1 may be purchased as is or in the form of their hydrochlorides In methods for preparing compounds of the present invention, reaction conditions such as types and amounts of solvent, base, and reactants are not limited to those as mentioned in the above. It is understood that a person of ordinary skill in the art can easily prepare compounds of the present invention through any combination of synthesis methods as described in the specification or as disclosed in known documents.

According to another aspect of the present invention, there is provided a pharmaceutical composition comprising a therapeutically effective amount of a 1,2,4-triazole derivative tion of the present invention is useful in treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly useful in treating osteoarthritis and rheumatoid arthritis which require high dosage of nonsteroidal anti-inflammatory agents.

The pharmaceutical composition of the present invention can be administered in the form of an adult dosage of 1 mg/day to 1000 mg/day of the compound of formula 1. An adequate dosage is determined depending on the degree of disease severity.

According to yet another aspect of the present invention, there is provided a pharmaceutical composition comprising a therapeutically effective amount of a 1,2,4-triazole derivative of formula 1 or a non-toxic salt thereof and a pharmaceutically acceptable carrier for the treatment of cancers and dementia.

Recently, it was reported that nonsteroidal anti-inflammatory agents are effective in the treatment of large intestine cancer [*European Journal of Cancer*, Vol 37, p2302, 2001], prostate cancer [*Urology*, Vol 58, p127, 2001], and dementia [*Exp. Opin. Invest Drugs*, Vol 9, p671, 2000]. Therefore, it is understood that the pharmaceutical composition of the present invention as a nonsteroidal anti-inflammatory agent can also be used for the treatment of these diseases.

The pharmaceutical composition for the treatment of cancers and dementia of the present invention can be administered in the form of an adult dosage of 1 mg/day to 1000 mg/day of the compound of formula 1 or a non-toxic salt thereof. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscular injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

A plasticizer suitable for the coating agent is citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed in Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustration and thus the present invention is not limited to or by them.

EXAMPLE 1

4-fluorobenzoylisocyanate

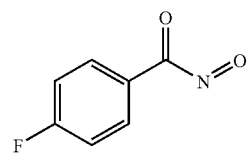

Formula 6

1.5 g of 4-fluorobenzamide was dissolved in 20 ml of dichloromethane and 2.3 ml of oxalyl chloride was slowly added thereto at room temperature, and then the mixutre was heated and refluxed for 16 hours. When the reaction was completed, the reaction mixture was cooled to room temperature and the solvent was distilled under reduced pressure to produce the titled compound as a oil. Without purification processes, next process was proceeded.

Mass(LOW EI)=165.0

EXAMPLE 2

4-methoxybenzoylisocyanate

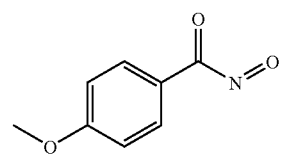

Formula 7

The titled compound as a liquid was prepared in the same manner as in Example 1 except using 2.0 g of 4-methoxybenzamide instead of 4-fluorobenzamide.

Mass(LOW EI)=177.04

EXAMPLE 3

4-ethoxybenzoylisocyanate

Formula 8

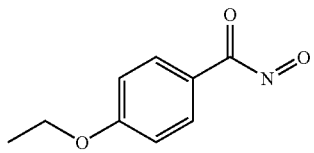

The titled compound as a liquid was prepared in the same manner as in Example 1 except using 2.0 g of 4-ethoxybenzamide instead of 4-fluorobenzamide.
Mass(LOW EI)=191.04

EXAMPLE 4

4-bromobenzoylisocyanate

Formula 9

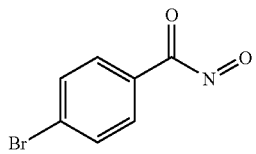

The titled compound as a liquid was prepared in the same manner as in Example 1 except using 2.0 g of 4-bromobenzamide instead of 4-fluorobenzamide.
Mass(LOW EI)=225.0

EXAMPLE 5

3-fluoro-4-methoxybenzoylisocyanate

Formula 10

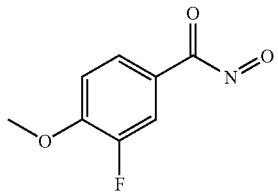

The titled compound as a liquid was prepared in the same manner as in Example 1 except using 2.0 g of 3-fluoro-4-methoxybenzamide instead of 4-fluorobenzamide.
Mass(LOW EI)=195.0

EXAMPLE 6

1-benzoyl-3-(4-aminosulfonylbenzenehydrazinyl)-urea

Formula 11

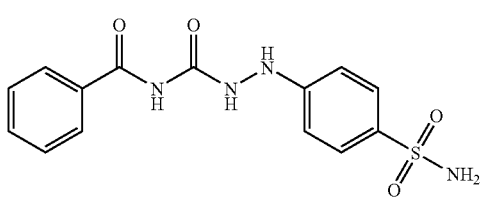

3.1 g of benzoylisocyanate was dissolved in 20 ml of DMF and then 1 eq of 4-aminosulfonylbenzenehydrazine hydrochloride and 2 eq of potassium carbonate were added thereto and stirred for 4 hours at room temperature. When the reaction was completed, 100 ml of water was added thereto to form yellow precipitate. The yellow precipitate was washed with 30 ml of EA/n-Hex(1/6) to give 4.70 g of the titled compound as a pale yellow solid (yield 66%).
Mass(LOW EI)=334.0

EXAMPLE 7

1-(4-fluorobenzoyl)-3-(4-aminosulfonylbenzenehydrazinyl)-urea

Formula 12

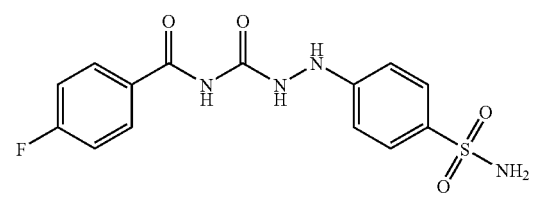

2.85 g (yield 67%) of the titled compound as a yellow solid was prepared in the same manner as in Example 6 except using 2.0 g of 4-fluorobenzoylisocyanate instead of benzoylisocyanate.
Mass(LOW EI)=352.0

EXAMPLE 8

1-(4-methoxybenzoyl)-3-(4-aminosulfonylbenzenehydrazinyl)-urea

Formula 13

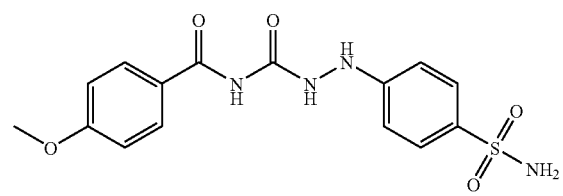

4.45 g (yield 72%) of the titled compound as a yellow solid was prepared in the same manner as in Example 6 except using 3.0 g of 4-methoxybenzoyl isocyanate instead of benzoylisocyanate.
Mass(LOW EI)=364.0

EXAMPLE 9

1-(4-bromobenzoyl)-3-(4-aminosulfonylbenzenehydrazinyl)-urea

Formula 14

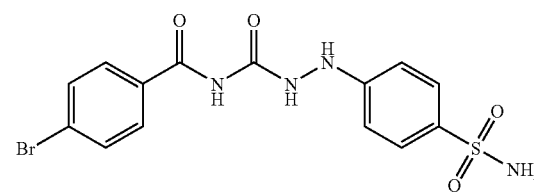

3.50 g (yield 63%) of the titled compound as a yellow solid was prepared in the same manner as in Example 6 except using 3.0 g of 4-bromobenzoylisocyanate instead of benzoylisocyanate.
Mass(LOW EI)=412.0

EXAMPLE 10

1-(4-ethoxybenzoyl)-3-(4-aminosulfonylbenzenehydrazinyl)-urea

Formula 15

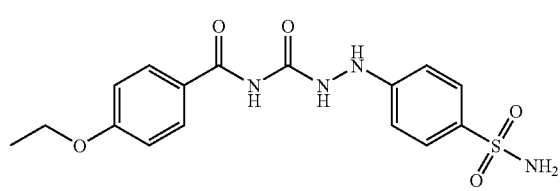

4.50 g (yield 70%) of the titled compound as a yellow solid was prepared in the same manner as in Example 6 except using 3.0 g of 4-ethoxybenzoylisocyanate instead of benzoylisocyanate.

Mass(LOW EI)=378.0

EXAMPLE 11

1-(3-fluoro-4-methoxybenzoyl)-3-(4-aminosulfonylbenzenehydrazinyl)-urea

Formula 16

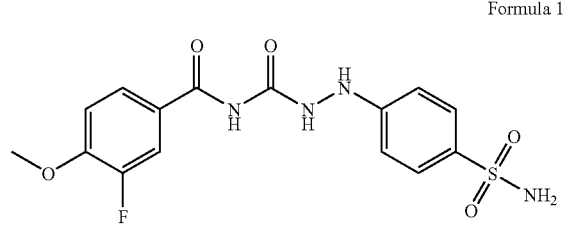

3.20 g (yield 55%) of the titled compound as a yellow solid was prepared in the same manner as in Example 6 except using 3.0 g of 3-fluoro-4-methoxybenzoylisocyanate instead of benzoylisocyanate.

Mass(LOW EI)=382.0

EXAMPLE 12

1-benzoyl-3-(4-aminosulfonylbenzenehydrazinyl)-thiourea

Formula 17

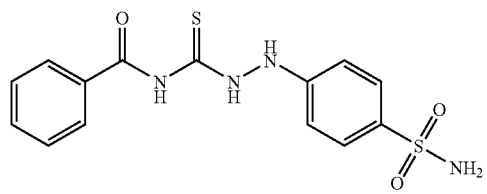

4.50 g (yield 70%) of the titled compound as a yellow solid was prepared in the same manner as in Example 6 except using 3.0 g of benzoylisothiocyanate instead of benzoylisocyanate.

Mass(LOW EI)=350.0

EXAMPLE 13

1-benzoyl-3-(4-methanesulfonylbenzenehydrazinyl)-urea

Formula 18

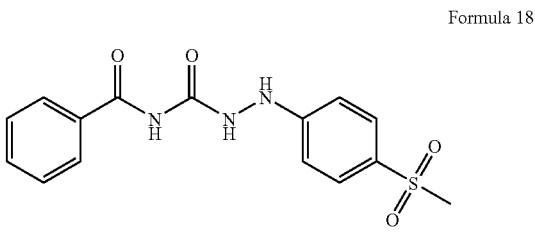

4.20 g (yield 79%) of the titled compound as a yellow solid was prepared in the same manner as in Example 6 except using 3.0 g of 4-methanesulfonylbenzenehydrazine hydrochloride instead of 4-aminosulfonylbenzenehydrazine hydrochloride.

Mass(LOW EI)=330.0

EXAMPLE 14

1-(4-methoxybenzoyl)-3-(4-methanesulfonylbenzenehydrazinyl)-urea

Formula 19

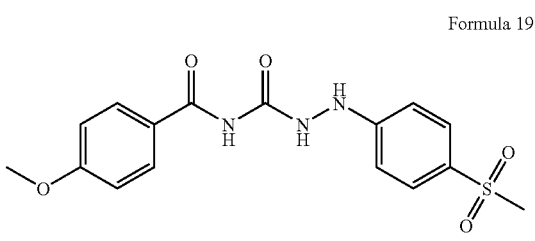

3.70 g (yield 60%) of the titled compound as a yellow solid was prepared in the same manner as in Example 13 except using 3.0 g of 4-methoxybenzoylisocyanate instead of benzoylisocyanate.

Mass(LOW EI)=363.0

EXAMPLE 15

4-(3-hydroxy-5-phenyl-1,2,4-triazole-1-yl)-benzenesulfonamide

Formula 20

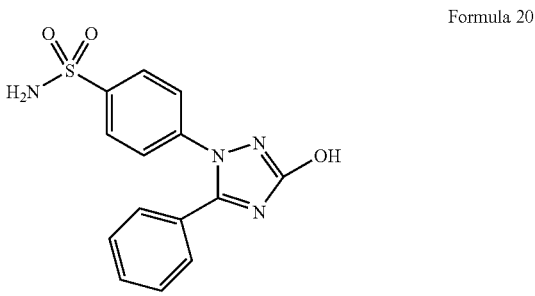

40 ml of 10% KOH solution was slowly added to 5 g of 1-benzoyl-3-(4-aminosulfonylbenzenehydrazinyl)-urea and then refluxed for 10 hours. When the reaction was completed, the resultant was poured into 100 ml of cold water to form a white solid precipitate at the bottom of the solution. The white precipitate was filtered and then washed with 50 ml of cold water and 50 ml of IPA (1× each) to give 3.60 g (yield 75%) of the titled compound as a pale yellow solid.

¹H NMR (DMSO-d6, 400 MHz)

7.40-7.50 (m, 7H), 7.55 (d, 2H, J=8.7 Hz), 7.88 (d, 2H, J=8.7 Hz)

EXAMPLE 16

4-[3-hydroxy-5-(4-methoxyphenyl)-1,2,4-triazole-1-yl]-benzenesulfonamide

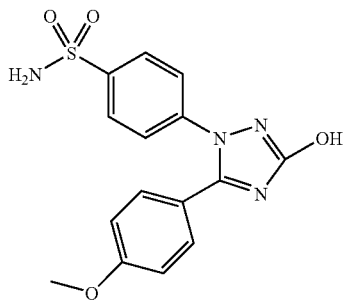

Formula 21

3.8 g (yield 75%) of the titled compound as a yellow solid was prepared in the same manner as in Example 15 except using 5.1 g of 1-(4-methoxybenzoyl)-3-(4-aminosulfonyl-benzenehydrazinyl)-urea instead of 1-benzoyl-3-(4-aminosulfonylbenzenehydrazinyl)-urea.

¹H NMR (DMSO-d6, 400 MHz)

3.88 (s, 3H), 7.00 (d, 2H, J=8.9 Hz), 7.30 (d, 2H, J=8.9 Hz), 7.40 (s, 2H), 7.60 (d, 2H, J=8.6 Hz), 7.95 (d, 2H, J=8.6 Hz)

EXAMPLE 17

4-[3-hydroxy-5-(4-ethoxyphenyl)-1,2,4-triazole-1-yl]-benzenesulfonamide

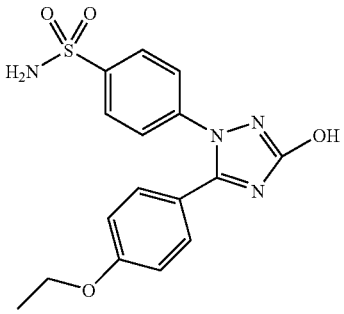

Formula 22

3.8 g (yield 65%) of the titled compound as a yellow solid was prepared in the same manner as in Example 15 except using 5.0 g of 1-(4-ethoxybenzoyl)-3-(4-aminosulfonylbenzenehydrazinyl)-urea instead of 1-benzoyl-3-(4-aminosulfonylbenzenehydrazinyl)-urea.

¹H NMR (DMSO-d6, 400 MHz)

1.40 (t, 3H, J=6.9 Hz), 3.88 (q, 2H, J=6.9 Hz), 4.35 (q, 2H, J=6.9 Hz), 7.00 (d, 2H, J=8.9 Hz), 7.30 (d, 2H, J=8.9 Hz), 7.40 (s, 2H), 7.60 (d, 2H, J=8.6 Hz), 7.95 (d, 2H, J=8.6 Hz)

EXAMPLE 18

4-[3-hydroxy-5-(4-fluorophenyl)-1,2,4-triazole-1-yl]-benzenesulfonamide

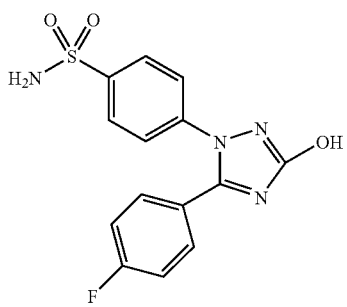

Formula 23

4.8 g (yield 75%) of the titled compound as a yellow solid was prepared in the same manner as in Example 15 except using 6.6 g of 1-(4-fluorobenzoyl)-3-(4-aminosulfonylbenzenehydrazinyl)-urea instead of 1-benzoyl-3-(4-aminosulfonylbenzenehydrazinyl)-urea.

¹H NMR (DMSO-d6, 400 MHz)

6.90 (d, 2H, J=8.9 Hz), 7.20 (d, 2H, J=8.9 Hz), 7.40 (s, 2H), 7.60 (d, 2H, J=8.6 Hz), 7.95 (d, 2H, J=8.6 Hz)

EXAMPLE 19

4-[3-hydroxy-5-(4-bromophenyl)-1,2,4-triazole-1-yl]-benzenesulfonamide

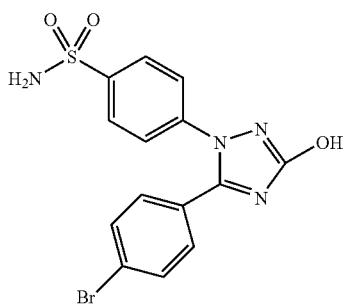

Formula 24

3.5 g (yield 61%) of the titled compound as a yellow solid was prepared in the same manner as in Example 15 except using 6.0 g of 1-(4-bromobenzoyl)-3-(4-aminosulfonylbenzenehydrazinyl)-urea instead of 1-benzoyl-3-(4-aminosulfonylbenzenehydrazinyl)-urea.

¹H NMR (DMSO-d6, 400 MHz)

7.30 (d, 2H, J=8.9 Hz), 7.40 (d, 2H, J=8.9 Hz), 7.45 (s, 2H), 7.60 (d, 2H, J=8.6 Hz), 7.95 (d, 2H, J=8.6 Hz)

EXAMPLE 20

4-[3-hydroxy-5-(3-fluoro-4-methoxyphenyl)-1,2,4-triazole-1-yl]-benzenesulfonamide

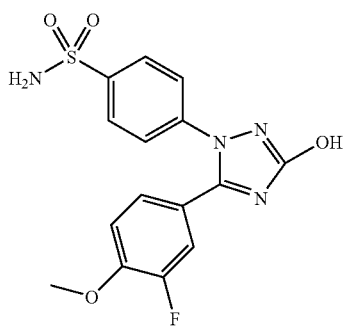

Formula 25

1.80 g (yield 70%) of the titled compound as a yellow solid was prepared in the same manner as in Example 15 except using 2.70 g of 1-(3-fluoro-4-methoxybenzoyl)-3-(4-aminosulfonylbenzenehydrazinyl)-urea instead of 1-benzoyl-3-(4-aminosulfonylbenzenehydrazinyl)-urea.

$^1$H NMR (DMSO-d6, 400 MHz)

3.95 (s, 3H), 7.15-7.25 (m, 2H), 7.30 (dd, 1H, J=1.8, 12.9 Hz), 7.50 (s, 2H), 7.55 (d, 2H, J=8.7 Hz), 7.90 (d, 2H, J=8.7 Hz)

EXAMPLE 21

4-(3-mercapto-5-phenyl-1,2,4-triazole-1-yl)-benzenesulfonamide

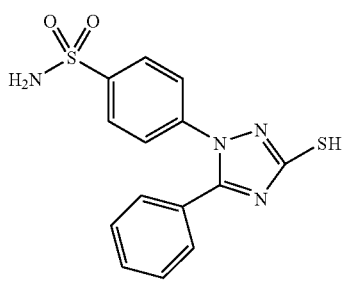

Formula 26

3.8 g (yield 65%) of the titled compound as a yellow solid was prepared in the same manner as in Example 15 except using 5.0 g of 1-benzoyl-3-(4-aminosulfonylbenzenehydrazinyl)-thiourea instead of 1-benzoyl-3-(4-aminosulfonylbenzenehydrazinyl)-urea.

$^1$H NMR (DMSO-d6, 400 MHz)

7.40-7.50 (m, 7H), 7.55 (d, 2H, J=8.7 Hz), 7.88 (d, 2H, J=8.7 Hz)

EXAMPLE 22

1-(4-methanesulfonylphenyl)-5-phenyl-1H-1,2,4-triazole-3-ol

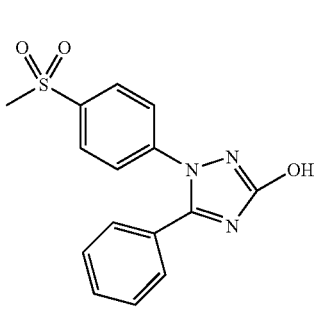

Formula 27

3.6 g (yield 65%) of the titled compound as a yellow solid was prepared in the same manner as in Example 15 except using 5.0 g of 1-benzoyl-3-(4-methanesulfonylbenzenehydrazinyl)-urea instead of 1-benzoyl-3-(4-aminosulfonylbenzenehydrazinyl)-urea.

$^1$H NMR (DMSO-d6, 400 MHz)

3.10 (s, 3H), 7.40-7.50 (m, 7H), 7.50 (d, 2H, J=8.7 Hz), 7.80 (d, 2H, J=8.7 Hz)

EXAMPLE 23

1-(4-methanesulfonylphenyl)-5-(4-methoxyphenyl)-1H-1,2,4-triazole-3-ol

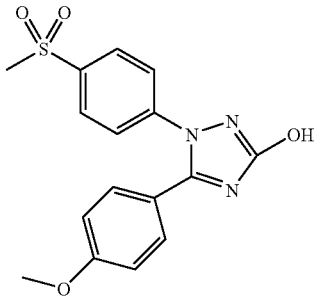

Formula 28

3.3 g (yield 69%) of the titled compound as a yellow solid was prepared in the same manner as in Example 15 except using 5.0 g of 1-(4-methoxybenzoyl)-3-(4-methanesulfonylbenzenehydrazinyl)-urea instead of 1-benzoyl-3-(4-aminosulfonylbenzenehydrazinyl)-urea.

$^1$H NMR (DMSO-d6, 400 MHz)

3.98 (s, 3H) 7.00 (d, 2H, J=8.9 Hz), 7.30 (d, 2H, J=8.9 Hz), 7.40 (s, 2H), 7.60 (d, 2H, J=8.6 Hz), 7.95 (d, 2H, J=8.6 Hz)

EXAMPLE 24

4-[3-methoxy-5-(4-methoxyphenyl)-1,2,4-triazole-1-yl]-benzenesulfonamide

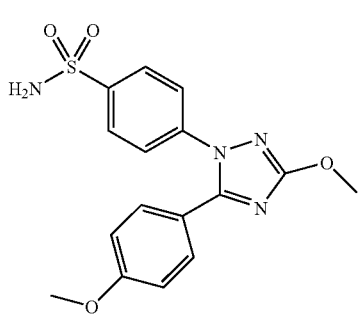

Formula 29

500 mg of 4-[3-hydroxy-5-(4-methoxyphenyl)-1,2,4-triazole-1-yl]-benzenesulfonamide prepared in the above Example 16, was dissolved in 10 ml of DMF and then 1.05 eq of NaH was slowly added thereto. Afterwards 1.5 eq of iodomethane was added to the mixture and then stirred for 3 hours at the same temperature. When the reaction was completed, the resultant was poured into 100 ml of cold water to form precipitate. The precipitate was filtered and then washed with 100 ml of cold ether and 100 ml of cold water (1× each) to give 385 mg (yield 75%) of the titled compound as a white solid.

$^1$H NMR (DMSO-d6, 400 MHz)

3.80 (s, 3H), 3.98 (s, 3H) 7.00 (d, 2H, J=8.9 Hz), 7.30 (d, 2H, J=8.9 Hz), 7.40 (s, 2H), 7.60 (d, 2H, J=8.6 Hz), 7.95 (d, 2H, J=8.6 Hz)

EXAMPLE 25

4-(3-methoxy-5-phenyl-1,2,4-triazole-1-yl)-benzenesulfonamide

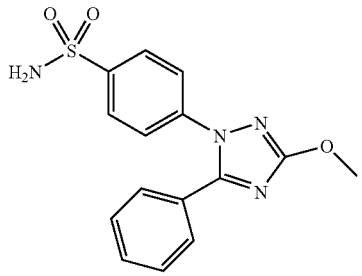

Formula 30

281 mg (yield 73%) of the titled compound as a yellow solid was prepared in the same manner as in Example 24 except using 300 mg of 4-(3-hydroxy-5-phenyl-1,2,4-triazole-1-yl)-benzenesulfonamide instead of 4-[3-hydroxy-5-(4-methoxyphenyl)-1,2,4-triazole-1-yl]-benzenesulfonamide.

$^1$H NMR (DMSO-d6, 400 MHz)

3.10 (s, 3H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 26

4-[3-methoxy-5-(4-fluorophenyl)-1,2,4-triazole-1-yl]-benzenesulfonamide

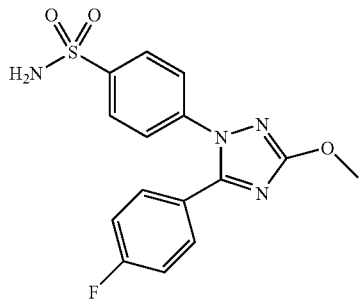

Formula 31

240 mg (yield 67%) of the titled compound as a yellow solid was prepared in the same manner as in Example 24 except using 300 mg of 4-[3-hydroxy-5-(4-fluorophenyl)-1,2,4-triazole-1-yl]-benzenesulfonamide instead of 4-[3-hydroxy-5-(4-methoxyphenyl)-1,2,4-triazole-1-yl]-benzenesulfonamide.

$^1$H NMR (DMSO-d6, 400 MHz)

3.80 (s, 3H), 7.30 (d, 2H, J=7.0 Hz), 7.45-7.60 (m, 6H), 8.00 (d, 2H, J=7.0 Hz)

EXAMPLE 27

4-[3-methoxy-5-(4-bromophenyl)-1,2,4-triazole-1-yl]-benzenesulfonamide

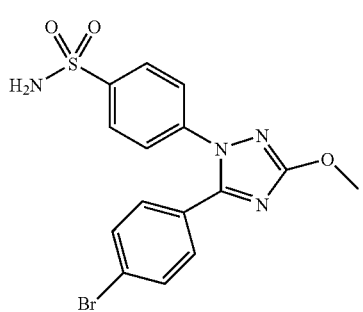

Formula 32

200 mg (yield 57%) of the titled compound as a yellow solid was prepared in the same manner as in Example 24 except using 300 mg of 4-[3-hydroxy-5-(4-bromophenyl)-1,2,4-triazole-1-yl]-benzenesulfonamide instead of 4-[3-hydroxy-5-(4-methoxyphenyl)-1,2,4-triazole-1-yl]-benzenesulfonamide.

$^1$H NMR (DMSO-d6, 400 MHz)

3.80 (s, 3H), 7.40 (d, 2H, J=7.0 Hz), 7.45-7.50 (m, 4H), 7.65 (d, 2H, J=8.7 Hz), 8.00 (d, 2H, J=8.7 Hz)

EXAMPLE 28

4-[3-methoxy-5-(3-fluoro-4-methoxyphenyl)-1,2,4-triazole-1-yl]-benzenesulfonamide

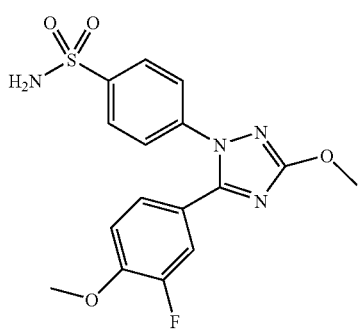

Formula 33

150 mg (yield 76%) of the titled compound as a yellow solid was prepared in the same manner as in Example 24 except using 200 mg of 4-[3-hydroxy-5-(3-fluoro-4-methoxyphenyl)-1,2,4-triazole-1-yl]-benzenesulfonamide instead of 4-[3-hydroxy-5-(4-methoxyphenyl)-1,2,4-triazole-1-yl]-benzenesulfonamide.

$^1$H NMR (DMSO-d6, 400 MHz)

3.80 (s, 3H), 4.90 (s, 3H), 7.15-22 (m, 2H), 7.30 (dd, J=1.8, 12.9 Hz), 7.50 (s, 2H), 7.55 (d, 2H, J=8.7 Hz), 7.90 (d, 2H, J=8.7 Hz)

EXAMPLE 29

4-(3-methylthio-5-phenyl-1,2,4-triazole-1-yl)-benzenesulfonamide

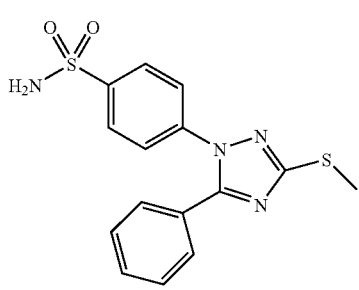

Formula 34

120 mg (yield 61%) of the titled compound as a yellow solid was prepared in the same manner as in Example 24 except using 200 mg of 4-(3-mercapto-5-phenyl-1,2,4-triazole-1-yl)-benzenesulfonamide instead of 4-[3-hydroxy-5-(4-methoxyphenyl)-1,2,4-triazole-1-yl]-benzenesulfonamide.

$^1$H NMR (DMSO-d6, 400 MHz)

3.10 (s, 3H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 30

4-[3-ethoxy-5-(4-methoxyphenyl)-1,2,4-triazole-1-yl]-benzenesulfonamide

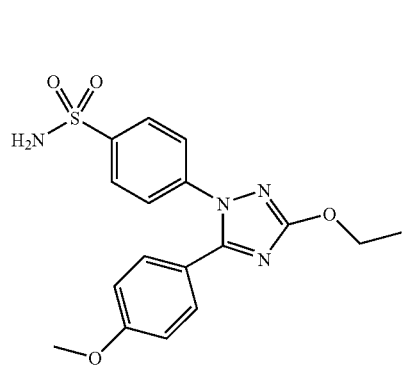

Formula 35

200 mg (yield 63%) of the titled compound as a yellow solid was prepared in the same manner as in Example 24 except using iodoethane instead of iodomethane.

$^1$H NMR (DMSO-d6, 400 MHz)

1.50 (t, 3H, J=7.0 Hz), 3.80 (s, 3H), 4.20 (q, 2H, J=7.0 Hz), 6.90 (d, 2H, J=8.6 Hz), 7.25 (d, 2H, J=8.6 Hz), 7.45 (s, 2H), 7.60 (d, 2H, J=8.3 Hz), 7.95 (d, 2H, J=8.3 Hz)

EXAMPLE 31

4-(3-ethoxy-5-phenyl-1,2,4-triazole-1-yl)-benzenesulfonamide

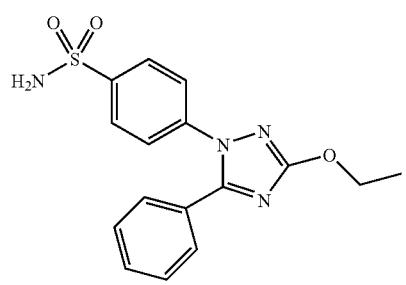

Formula 36

160 mg (yield 50%) of the titled compound as a yellow solid was prepared in the same manner as in Example 25 except using iodoethane instead of iodomethane.

$^1$H NMR (DMSO-d6, 400 MHz)

1.50 (t, 3H, J=7.0 Hz), 4.20 (q, 2H, J=7.0 Hz), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 32

4-[3-ethoxy-5-(4-fluorophenyl)-1,2,4-triazole-1-yl]-benzenesulfonamide

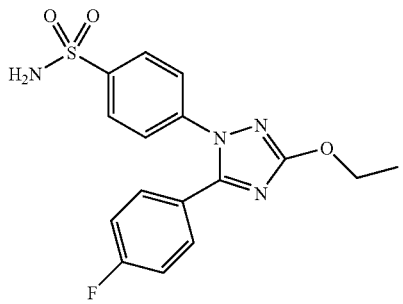

Formula 37

200 mg (yield 63%) of the titled compound as a yellow solid was prepared in the same manner as in Example 26 except using iodoethane instead of iodomethane.

$^1$H NMR (DMSO-d6, 400 MHz)

1.45 (t, 3H, J=6.7 Hz), 4.20 (q, 2H, J=6.7 Hz), 7.30 (d, 2H, J=7.0 Hz), 7.45-7.60 (m, 6H), 8.00 (d, 2H, J=7.0 Hz)

EXAMPLE 33

4-[3-ethoxy-5-(3-fluoro-4-methoxyphenyl)-1,2,4-triazole-1-yl]-benzenesulfonamide

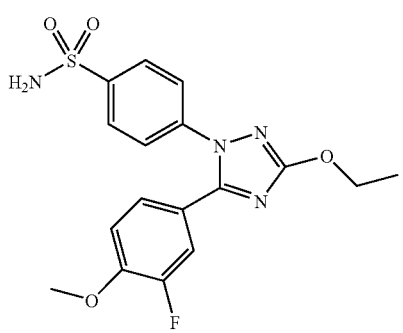

Formula 38

100 mg (yield 45%) of the titled compound as a yellow solid was prepared in the same manner as in Example 28 except using iodoethane instead of iodomethane.

$^1$H NMR (DMSO-d6, 400 MHz)

1.35 (t, 3H, J=6.1 Hz), 3.80 (s, 3H), 4.84 (q, 2H, J=6.1 Hz), 7.15-22 (m, 2H), 7.30 (dd, J=1.8, 12.9 Hz), 7.50 (s, 2H), 7.55 (d, 2H, J=8.7 Hz), 7.90 (d, 2H, J=8.7 Hz)

EXAMPLE 34

4-(3-ethylthio-5-phenyl-1,2,4-triazole-1-yl)-benzenesulfonamide

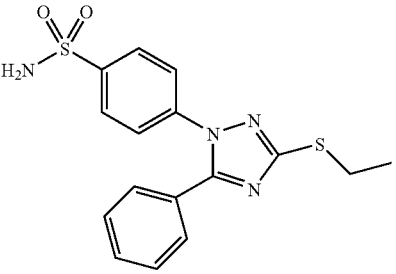

Formula 39

110 mg (yield 55%) of the titled compound as a yellow solid was prepared in the same manner as in Example 29 except using iodoethane instead of iodomethane.

$^1$H NMR (DMSO-d6, 400 MHz)

1.50 (t, 3H, J=7.0 Hz), 4.20 (q, 2H, J=7.0 Hz), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 35

4-[3-propoxy-5-(4-methoxyphenyl)-1,2,4-triazole-1-yl]-benzenesulfonamide

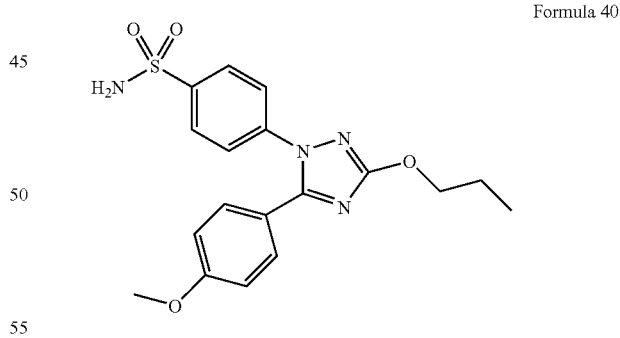

Formula 40

160 mg (yield 51%) of the titled compound as a yellow solid was prepared in the same manner as in Example 24 except using iodopropane instead of iodomethane.

$^1$H NMR (DMSO-d6, 400 MHz)

1.0 (t, 3H, J=7.3 Hz), 1.80 (dt, 2H, J=6.5, 7.3 Hz), 3.80 (s, 3H), 4.25 (t, 2H, J=6.5 Hz)1, 6.90 (d, 2H, J=8.6 Hz), 7.25 (d, 2H, J=8.6 Hz), 7.45 (s, 2H), 7.60 (d, 2H, J=8.3 Hz), 7.95 (d, 2H, J=8.3 Hz)

EXAMPLE 36

4-[3-propoxy-5-(4-fluorophenyl)-1,2,4-triazole-1-yl]-benzenesulfonamide

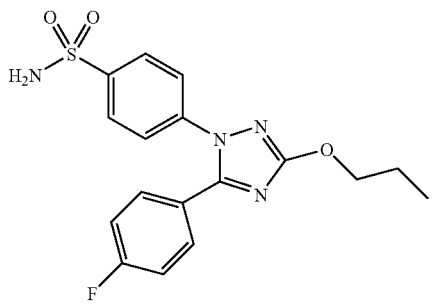

Formula 41

200 mg (yield 63%) of the titled compound as a yellow solid was prepared in the same manner as in Example 26 except using iodopropane instead of iodomethane.

$^1$H NMR (DMSO-d6, 400 MHz)

1.0 (t, 3H, J=7.3 Hz), 1.80 (dt, 2H, J=6.5, 7.3 Hz), 4.25 (t, 2H, J=6.5 Hz), 7.30 (d, 2H, J=7.0 Hz), 7.45-7.60 (m, 6H), 8.00 (d, 2H, J=7.0 Hz)

EXAMPLE 37

4-[3-cyclopentyloxy-5-(4-methoxyphenyl)-1,2,4-triazole-1-yl]-benzenesulfonamide

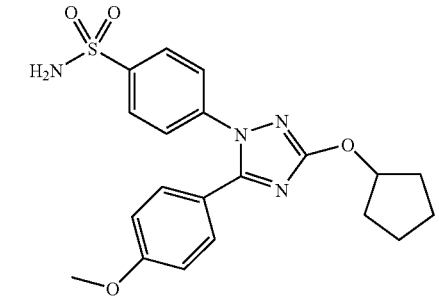

Formula 42

150 mg (yield 45%) of the titled compound as a yellow solid was prepared in the same manner as in Example 24 except using cyclopentyl bromide instead of methy liodide.

$^1$H NMR (DMSO-d6, 400 MHz)

1.60-2.00 (m, 8H), 3.80 (s, 3H), 5.10 (t, 1H, J=4.8 Hz), 7.00 (d, 2H, J=8.7 Hz), 7.30 (d, 2H, J=8.7 Hz), 7.45 (s, 2H), 7.60 (d, 2H, J=6.7 Hz), 8.00 (d, 2H, J=6.7 Hz)

EXAMPLE 38

4-[3-cyclopentyloxy-5-(4-fluorophenyl)-1,2,4-triazole-1-yl]-benzenesulfonamide

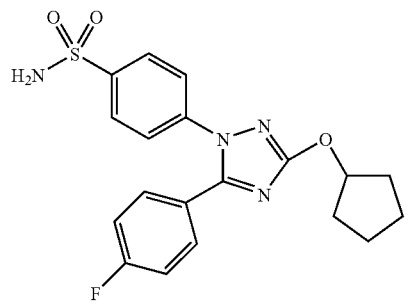

Formula 43

100 mg (yield 43%) of the titled compound as a yellow solid was prepared in the same manner as in Example 26 except using cyclopentyl bromide instead of iodomethane.

$^1$H NMR (DMSO-d6, 400 MHz)

1.60-2.00 (m, 8H), 3.80 (s, 3H), 5.10 (t, 1H, J=4.8 Hz), 7.30 (d, 2H, J=7.0 Hz), 7.45-7.60 (m, 6H), 8.00 (d, 2H, J=7.0 Hz)

EXAMPLE 39

4-[3-cyclohexyloxy-5-(4-methoxyphenyl)-1,2,4-triazole-1-yl]-benzenesulfonamide

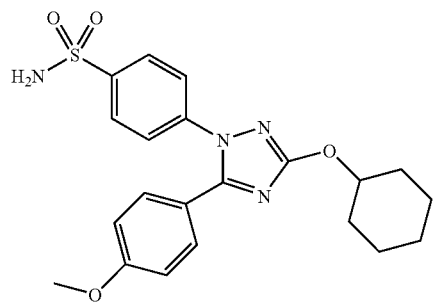

Formula 44

165 mg (yield 47%) of the titled compound as a yellow solid was prepared in the same manner as in Example 24 except using cyclohexyl bromide instead of iodomethane.

$^1$H NMR (DMSO-d6, 400 MHz)

1.30 (bs, 2H), 1.50 (bs, 2H), 1.70 (bs, 2H), 2.00 (bs, 2H), 3.80 (s, 3H), 4.60 (bs, 1H), 7.00 (d, 2H, J=8.7 Hz), 7.30 (d, 2H, J=8.7 Hz), 7.45 (s, 2H), 7.60 (d, 2H, J=6.7 Hz), 8.00 (d, 2H, J=6.7 Hz)

EXAMPLE 40

4-[3-cyclohexyloxy-5-(4-fluorophenyl)-1,2,4-triazole-1-yl]-benzenesulfonamide

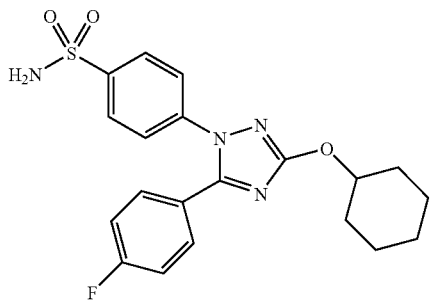

Formula 45

120 mg (yield 48%) of the titled compound as a yellow solid was prepared in the same manner as in Example 26 except using cyclohexyl bromide instead of iodomethane.

$^1$H NMR (DMSO-d6, 400 MHz)

1.30 (bs, 2H), 1.50 (bs, 2H), 1.70 (bs, 2H), 2.00 (bs, 2H), 3.80 (s, 3H), 4.60 (bs, 1H), 7.30 (d, 2H, J=7.0 Hz), 7.45-7.60 (m, 6H), 8.00 (d, 2H, J=7.0 Hz)

EXAMPLE 41

4-[3-cyanomethoxy-5-(4-methoxyphenyl)-1,2,4-triazole-1-yl]-benzenesulfonamide

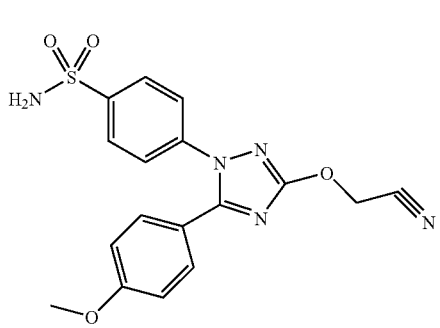

Formula 46

190 mg (yield 53%) of the titled compound as a yellow solid was prepared in the same manner as in Example 24 except using 1-iodoacetonitrile instead of methyliodide.

$^1$H NMR (DMSO-d6, 400 MHz)

5.20 (s, 2H), 7.00 (d, 2H, J=8.7 Hz), 7.30 (d, 2H, J=8.7 Hz), 7.45 (s, 2H), 7.60 (d, 2H, J=6.7 Hz), 8.00 (d, 2H, J=6.7 Hz)

EXAMPLE 42

4-[3-cyanomethoxy-5-(4-fluorophenyl)-1,2,4-triazole-1-yl]-benzenesulfonamide

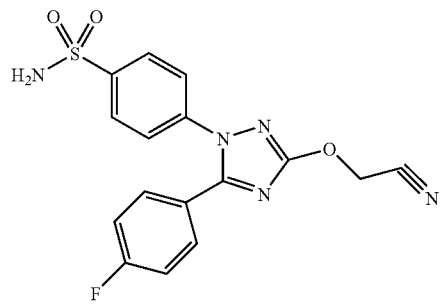

Formula 47

120 mg (yield 48%) of the titled compound as a yellow solid was prepared in the same manner as in Example 26 except using 1-iodoacetonitrile instead of iodomethane.

$^1$H NMR (DMSO-d6, 400 MHz)

5.20 (s, 2H), 7.30 (d, 2H, J=7.0 Hz), 7.45-7.60 (m, 6H), 8.00 (d, 2H, J=7.0 Hz)

EXAMPLE 43

4-[3-prop-2-ynyloxy-5-(4-methoxyphenyl)-1,2,4-triazole-1-yl]-benzenesulfonamide

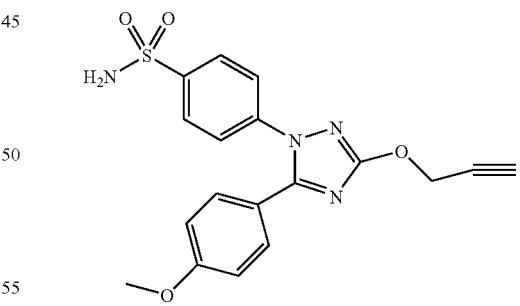

Formula 48

190 mg (yield 53%) of the titled compound as a yellow solid was prepared in the same manner as in Example 24 except using propagyl bromide instead of iodomethane.

$^1$H NMR (DMSO-d6, 400 MHz)

3.80 (s, 3H), 4.20 (s, 1H), 5.00 (s, 2H), 7.00 (d, 2H, J=8.7 Hz), 7.30 (d, 2H, J=8.7 Hz), 7.45 (s, 2H), 7.60 (d, 2H, J=6.7 Hz), 8.00 (d, 2H, J=6.7 Hz)

EXAMPLE 44

4-[3-prop-2-ynyloxy-5-(4-fluorophenyl)-1,2,4-triazole-1-yl]-benzenesulfonamide

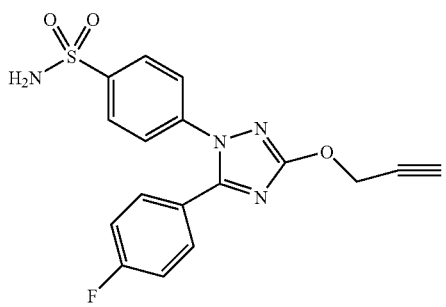

Formula 49

80 mg (yield 34%) of the titled compound as a yellow solid was prepared in the same manner as in Example 26 except using propagyl bromide instead of methyliodide.

$^1$H NMR (DMSO-d6, 400 MHz)

4.20 (s, 1H), 5.00 (s, 2H) 7.30 (d, 2H, J=7.0 Hz), 7.45-7.60 (m, 6H), 8.00 (d, 2H, J=7.0 Hz)

EXAMPLE 45

4-(3-prop-2-ynylthio-5-phenyl-1,2,4-triazole-1-yl)-benzenesulfonamide

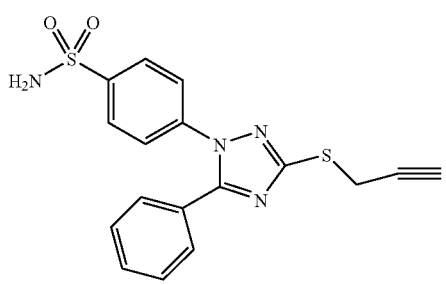

Formula 50

80 mg (yield 34%) of the titled compound as a yellow solid was prepared in the same manner as in Example 29 except using propagyl bromide instead of iodomethane.

$^1$H NMR (DMSO-d6, 400 MHz)

4.20 (s, 1H), 5.00 (s, 2H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 46

4-[3-isopropoxy-5-(4-methoxyphenyl)-1,2,4-triazole-1-yl]-benzenesulfonamide

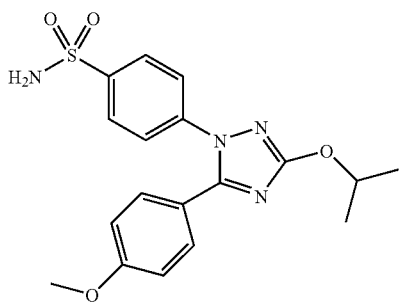

Formula 51

210 mg (yield 65%) of the titled compound as a yellow solid was prepared in the same manner as in Example 24 except using 2-iodopropane instead of iodomethane.

$^1$H NMR (DMSO-d6, 400 MHz)

1.20 (d, 6H, J=5.9 Hz), 3.80 (s, 3H), 4.95 (t, 1H, J=5.9 Hz), 5.15 (bs, 2H), 6.75 (d, 2H, J=8.8 Hz), 7.35 (d, 2H, J=8.8 Hz), 7.55 (d, 2H, J=8.5 Hz), 7.95 (d, 2H, J=8.5 Hz)

EXAMPLE 47

4-(3-isopropoxy-5-phenyl-1,2,4-triazole-1-yl)-benzenesulfonamide

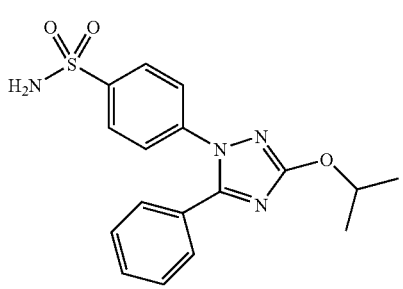

Formula 52

135 mg (yield 48%) of the titled compound as a yellow solid was prepared in the same manner as in Example 25 except using 2-iodopropane instead of iodomethane.

$^1$H NMR (DMSO-d6, 400 MHz)

1.20 (d, 6H, J=5.9 Hz), 4.95 (t, 1H, J=5.9 Hz), 5.15 (bs, 2H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 48

4-[3-isopropoxy-5-(4-fluorophenyl)-1,2,4-triazole-1-yl]-benzenesulfonamide

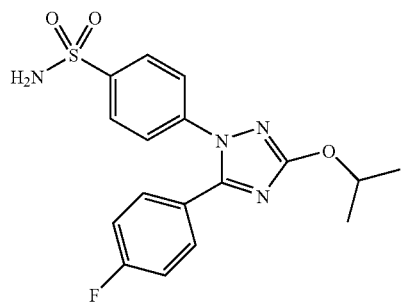

Formula 53

200 mg (yield 63%) of the titled compound as a yellow solid was prepared in the same manner as in Example 26 except using 2-iodopropane instead of iodomethane.

$^1$H NMR (DMSO-d6, 400 MHz)

1.20 (d, 6H, J=5.9 Hz), 4.95 (t, 1H, J=5.9 Hz), 5.15 (bs, 2H), 7.30 (d, 2H, J=7.0 Hz), 7.45-7.60 (m, 6H), 8.00 (d, 2H, J=7.0 Hz)

EXAMPLE 49

4-(3-isopropylthio-5-phenyl-1,2,4-triazole-1-yl)-benzenesulfonamide

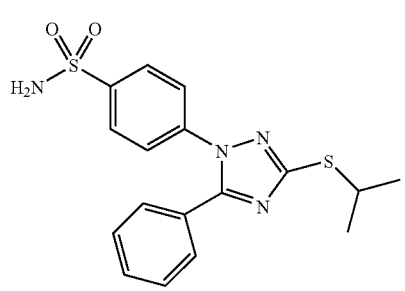

Formula 54

110 mg (yield 55%) of the titled compound as a yellow solid was prepared in the same manner as in Example 29 except using 2-iodopropane instead of iodomethane.

$^1$H NMR (DMSO-d6, 400 MHz)

1.20 (d, 6H, J=5.9 Hz), 4.95 (t, 1H, J=5.9 Hz), 5.15 (bs, 2H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 50

4-[3-benzyloxy-5-(3-fluoro-4-methoxyphenyl)-1,2,4-triazole-1-yl]-benzenesulfonamide

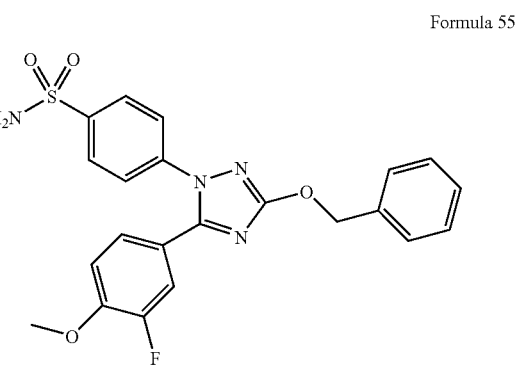

Formula 55

100 mg (yield 35%) of the titled compound as a yellow solid was prepared in the same manner as in Example 28 except using benzyl bromide instead of iodomethane.

$^1$H NMR (DMSO-d6, 400 MHz)

3.85 (s, 3H), 4.90 (s, 2H), 5.45 (s, 2H), 6.85 (t, 1H, J=8.7 Hz), 7.20 (d, 1H, J=8.3 hz), 7.30-7.45 (m, 3H), 7.50 (m, 4H), 8.05 (d, 2H, J=8.7 Hz)

EXAMPLE 51

4-(3-benzyloxy-5-phenyl-1,2,4-triazole-1-yl)-benzenesulfonamide

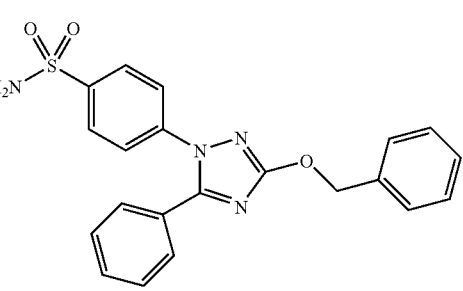

Formula 56

140 mg (yield 55%) of the titled compound as a yellow solid was prepared in the same manner as in Example 25 except using benzyl bromide instead of iodomethane.

Mass (Low EI)=406.0

EXAMPLE 52

4-[3-allyloxy-5-(4-methoxyphenyl)-1,2,4-triazole-1-yl]-benzenesulfonamide

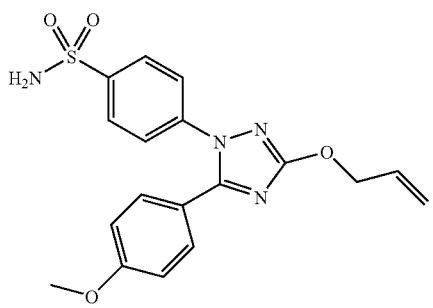

Formula 57

150 mg (yield 64%) of the titled compound as a yellow solid was prepared in the same manner as in Example 24 except using allyl bromide instead of iodomethane.

$^1$H NMR (CDCl3, 400 MHz)

3.80 (s, 3H), 4.80 (dt, 2H, J=1.5, 5.5 Hz), 5.00 (s, 2H), 5.40 (dd, 1H, J=1.3, 10.4 Hz), 5.60 (dd, 1H, J=1.3, 15.7 Hz), 6.10-6.20 (m, 1H), 6.75 (d, 2H, J=8.8 Hz), 7.35 (d, 2H, J=8.8 Hz), 7.55 (d, 2H, J=8.5 Hz), 7.95 (d, 2H, J=8.5 Hz)

EXAMPLE 53

4-(3-allyloxy-5-phenyl-1,2,4-triazole-1-yl)-benzenesulfonamide

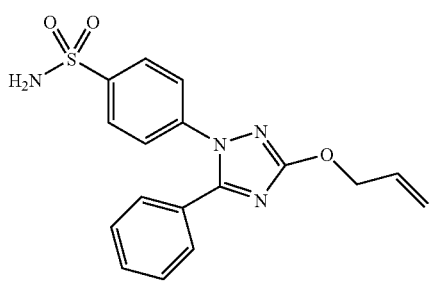

Formula 58

125 mg (yield 58%) of the titled compound as a yellow solid was prepared in the same manner as in Example 25 except using allyl bromide instead of iodomethane.

$^1$H NMR (CDCl3, 400 MHz)

4.80 (dt, 2H, J=1.5, 5.5 Hz), 5.00 (s, 2H), 5.40 (dd, 1H, J=1.3, 10.4 Hz), 5.60 (dd, 1H, J=1.3, 15.7 Hz), 6.10-6.20 (m, 1H), 7.40-7.45 (m, 2H), 7.47 (s, 2H). 7.48-7.52 (m, 3H), 7.58 (d, 2H, J=8.7 Hz), 7.90 (d, 2H, J=8.7 Hz)

EXAMPLE 54

4-[3-allyloxy-5-(4-fluorophenyl)-1,2,4-triazole-1-yl]-benzenesulfonamide

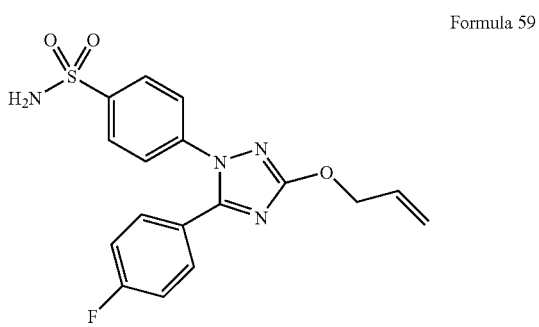

Formula 59

200 mg (yield 63%) of the titled compound as a yellow solid was prepared in the same manner as in Example 26 except using allyl bromide instead of iodomethane.

$^1$H NMR (DMSO-d6, 400 MHz)

4.80 (dt, 2H, J=1.5, 5.5 Hz), 5.40 (dd, 1H, J=1.3, 10.4 Hz), 5.60 (dd, 1H, J=1.3, 15.7 Hz), 6.10-6.20 (m, 1H), 7.30 (d, 2H, J=7.0 Hz), 7.45-7.60 (m, 6H), 8.00 (d, 2H, J=7.0 Hz)

EXAMPLE 55

4-[3-(2,2,2-trifluoroethoxy)-5-(4-methoxyphenyl)-1,2,4-triazole-1-yl]-benzenesulfonamide

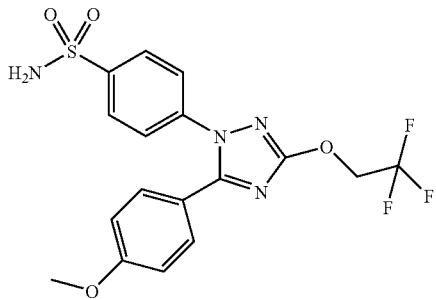

Formula 60

90 mg (yield 34%) of the titled compound as a yellow solid was prepared in the same manner as in Example 24 except using 1,1,1-trifluoro-2-bromoethane instead of iodomethane.

$^1$H NMR (DMSO-d6, 400 MHz)

3.80 (s, 3H), 4.80 (q, 2H, J=8.2 Hz), 6.75 (d, 2H, J=8.8 Hz), 7.35 (d, 2H, J=8.8 Hz), 7.55 (d, 2H, J=8.5 Hz), 7.95 (d, 2H, J=8.5 Hz)

EXAMPLE 56

4-[3-(2,2,2-trifluoroethoxy)-5-(4-fluorophenyl)-1,2,4-triazole-1-yl]-benzenesulfonamide

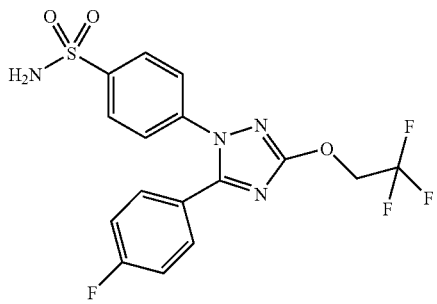

Formula 61

85 mg (yield 54%) of the titled compound as a yellow solid was prepared in the same manner as in Example 26 except using 1,1,1-trifluoro-2-bromoethane instead of iodomethane.

¹H NMR (DMSO-d6, 400 MHz)

4.80 (q, 2H, J=8.2 Hz), 7.30 (d, 2H, J=7.0 Hz), 7.45-7.60 (m, 6H), 8.00 (d, 2H, J=7.0 Hz)

EXAMPLE 57

4-[3-(2-chloroethoxy)-5-phenyl-1,2,4-triazole-1-yl]-benzenesulfonamide

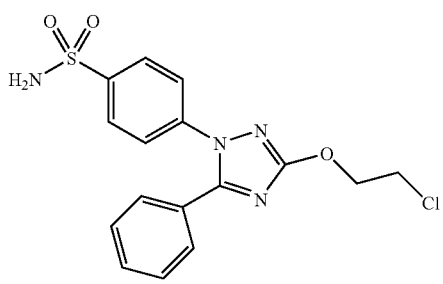

Formula 62

106 mg (yield 48%) of the titled compound as a yellow solid was prepared in the same manner as in Example 25 except using 2-chloro-1-iodoethane instead of iodomethane.

Mass (LOW EI)=364.1

EXAMPLE 58

4-[3-cyclopropoxy-5-phenyl-1,2,4-triazole-1-yl]-benzenesulfonamide

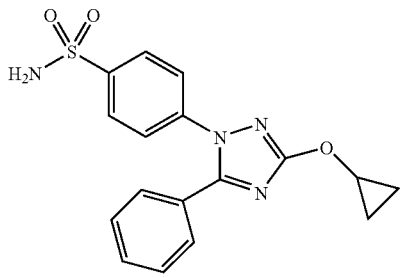

Formula 63

86 mg (yield 58%) of the titled compound as a yellow solid was prepared in the same manner as in Example 25 except using cyclopropyl bromide instead of iodomethane.

Mass (LOW EI)=356.2

EXAMPLE 59

1-(4-methanesulfonylphenyl)-3-methoxy-5-(4-methoxylphenyl)-1H-1,2,4-triazole

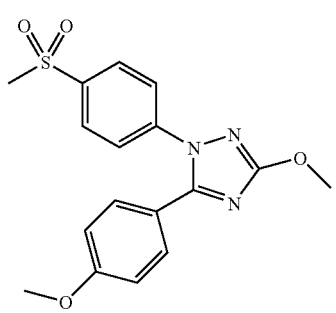

Formula 64

160 mg (yield 78%) of the titled compound as a yellow solid was prepared in the same manner as in Example 24 except using 200 mg of 1-(4-methanesulfonylphenyl)-5-(4-methoxyphenyl)-1H-1,2,4-triazole-3-ol instead of 4-[3-hydroxy-5-(4-methoxyphenyl)-1,2,4-triazole-1-yl]-benzenesulfonamide.

¹H NMR (DMSO-d6, 400 MHz)

3.10 (s, 3H), 3.98 (s, 6H) 7.00 (d, 2H, J=8.9 Hz), 7.30 (d, 2H, J=8.9 Hz), 7.60 (d, 2H, J=8.6 Hz), 7.95 (d, 2H, J=8.6 Hz)

EXAMPLE 60

1-(4-methanesulfonylphenyl)-3-methoxy-5-phenyl-1H-1,2,4-triazole

Formula 65

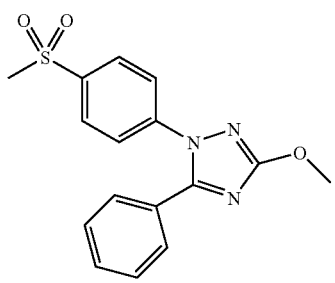

73 mg (yield 69%) of the titled compound as a yellow solid was prepared in the same manner as in Example 25 except using 100 mg of 1-(4-methanesulfonylphenyl)-5-phenyl-1H-1,2,4-triazole-3-ol instead of 4-(3-hydroxy-5-phenyl-1,2,4-triazole-1-yl)-benzenesulfonamide.

$^1$H NMR (DMSO-d6, 400 MHz)

3.10 (s, 3H), 3.98 (s, 3H), 7.40-7.45 (m, 2H), 7.48-7.52 (m, 3H), 7.58 (d, 2H, J=8.7 Hz), 7.90 (d, 2H, J=8.7 Hz)

EXAMPLE 61

1-(4-methanesulfonylphenyl)-3-ethoxy-5-(4-methoxyphenyl)-1H-1,2,4-triazole

Formula 66

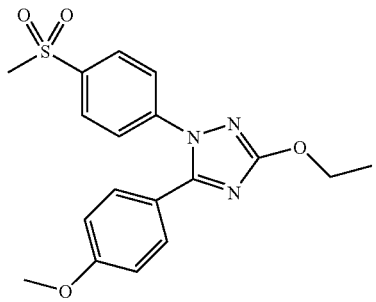

160 mg (yield 68%) of the titled compound as a yellow solid was prepared in the same manner as in Example 59 except using iodoethane instead of iodomethane.

Mass (LOW EI)=373.1

EXAMPLE 62

1-(4-methanesulfonylphenyl)-3-ethoxy-5-phenyl-1H-1,2,4-triazole

Formula 67

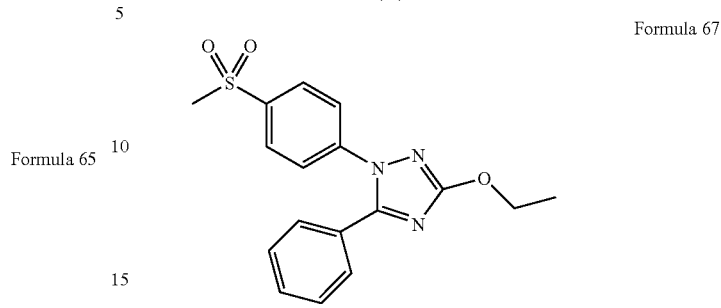

73 mg (yield 69%) of the titled compound as a yellow solid was prepared in the same manner as in Example 60 except using iodoethane instead of iodomethane.

Mass (LOW EI)=343.1

EXAMPLE 63

1-(4-methanesulfonylphenyl)-3-isopropoxy-5-(4-methoxyphenyl)-1H-1,2,4-triazole

Formula 68

120 mg (yield 58%) of the titled compound as a yellow solid was prepared in the same manner as in Example 59 except using 2-iodopropane instead of iodomethane.

Mass (LOW EI)=387.1

EXAMPLE 64

1-(4-methanesulfonylphenyl)-3-isopropoxy-5-phenyl-1H-1,2,4-triazole

Formula 69

63 mg (yield 59%) of the titled compound as a yellow solid was prepared in the same manner as in Example 60 except using 2-iodopropane instead of iodomethane.

Mass (LOW EI)=357.1

Experiments

1. Evaluation of Selective COX-2 Inhibitory Activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 Inhibitory Activity Using U-937

U-937 human lymphoma cells (Korean Cell Line Bank, Seoul, Korea, Accession Number: 21593) were cultured and centrifuged. The collected cells were diluted with HBSS (×1, Hank's balanced salt solution) to a concentration of $1 \times 10^6$ cells/ml. 1 ml of the dilute cell solution was placed into each well of 12-well plates. 5 µl of 1 µM solution of a test compound in DMSO and 5 µl of DMSO as a control were added to the wells. The wells were incubated in $CO_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 µl of the 1 mM solution of arachidonic acid was added to each well and incubated at $CO_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 Inhibitory Activity Using RAW 264.7 Cell Line $2 \times 10^6$ cells of RAW 264.7 cell line (Korean Cell Line Bank, Seoul, Korea, Accession Number: 40071) were inoculated into each well of 12-well plates. Each well was treated with 250 µM of aspirin and incubated at 37° C. for 2 hours. After the culture media were replaced with new culture media, the new culture media were treated with a test compound (10 nM) and incubated for 30 minutes. Then, each well was treated with interferon γ (100 units/ml) and lipopolysaccharide (LPS, 100 ng/ml) and incubated for 18 hours. The culture media were transferred to other test tubes. The concentration of PGE2 was quantified by means of the EIA kit (Cayman Chemicals).

2) Test Results

The test results are presented in Table 1 below. The percentages of the COX inhibition were calculated according to the following equation:

% Inhibition=(concentration of PGE2 in test compound-untreated sample−concentration of PGE2 in test compound-treated sample)/(concentration of PGE2 in test compound-untreated sample)×100

TABLE 1

| Samples | Cyclooxygenase (COX) Inhibition (%) | |
|---|---|---|
| | COX-1 (1 µM) | COX-2 (10 nM) |
| Reference (Valdecoxib) | 28.8 | 5.47 |
| Example 16 | 35.5 | 11.2 |
| Example 17 | 48.8 | 10.5 |
| Example 18 | 19.5 | 6.7 |
| Example 19 | 37.4 | 12.3 |
| Example 20 | 26.4 | 11.0 |
| Example 21 | 25.7 | 12.6 |

TABLE 1-continued

| Samples | Cyclooxygenase (COX) Inhibition (%) | |
|---|---|---|
| | COX-1 (1 µM) | COX-2 (10 nM) |
| Example 22 | 11.1 | 36.4 |
| Example 23 | 13.2 | 35.1 |
| Example 24 | 16.4 | 31.2 |
| Example 25 | 23.2 | 27.8 |
| Example 26 | 44.5 | 13.5 |
| Example 27 | 11.2 | 11.5 |
| Example 28 | 21.2 | 10.5 |
| Example 29 | 17.7 | 11.1 |
| Example 30 | 16.4 | 13.2 |
| Example 31 | 15.5 | 16.4 |
| Example 32 | 21.4 | 11.5 |
| Example 33 | 23.7 | 10.5 |
| Example 34 | 31.2 | 9.5 |
| Example 35 | 23.4 | 16.1 |
| Example 36 | 27.0 | 17.2 |
| Example 37 | 12.0 | 22.3 |
| Example 38 | 17.4 | 33.1 |
| Example 39 | 15.5 | 20.7 |
| Example 40 | 16.2 | 16.2 |
| Example 41 | 27.7 | 15.5 |
| Example 42 | 26.6 | 13.3 |
| Example 43 | 30.4 | 16.7 |
| Example 44 | 27.2 | 14.5 |
| Example 45 | 23.4 | 13.3 |
| Example 46 | 34.2 | 12.2 |
| Example 47 | 25.4 | 10.6 |
| Example 48 | 26.4 | 9.8 |
| Example 49 | 33.1 | 24.5 |
| Example 50 | 28.0 | 16.1 |
| Example 51 | 21.4 | 23.4 |
| Example 52 | 34.3 | 33.1 |
| Example 53 | 20.4 | 16.2 |
| Example 54 | 26.4 | 15.5 |
| Example 55 | 33.1 | 16.2 |
| Example 56 | 37.2 | 27.7 |
| Example 57 | 21.4 | 26.6 |
| Example 58 | 34.3 | 30.4 |
| Example 59 | 22.6 | 27.2 |
| Example 60 | 23.4 | 23.4 |
| Example 61 | 33.1 | 34.2 |
| Example 62 | 26.0 | 25.4 |
| Example 63 | 22.6 | 26.4 |
| Example 64 | 23.4 | 33.1 |

3) Evaluation

The in vitro test results about the percentages of the COX-1 and COX-2 inhibition are listed in Table 1.

As shown in Table 1, inhibition (%) ratios of COX-2 to COX-1 in Examples 16 to 64 were significantly higher than that in the reference, Valdecoxib. This indicates that selective inhibition of COX-2 to COX-1 of the present compound is superior to that of the reference.

INDUSTRIAL APPLICABILITY

As apparent from the above description, the 1,2,4-triazole derivative according to the present invention is an alternative drug for conventional nonsteroidal anti-inflammatory agents and is expected to be useful for treating patients with peptic ulcer disease, gastritis, regional enteritis, ulcerative colitis, diverticullitis, gastrorrhagia, or hypoprothrombinemia.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A 1,2,4-triazole derivative represented by formula 1:

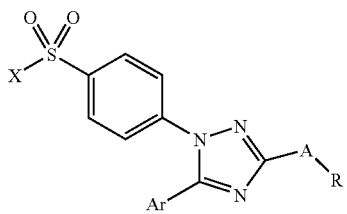

Formula 1 wherein:
X represents methyl or amino;
Ar represents phenyl or phenyl substituted with one or more radicals selected from the group consisting of $C_1$-$C_6$ alkoxy and halogen;
A represents O or S; and
R represents H, $C_1$-$C_6$ alkyl, trifluoro $C_1$-$C_6$ alkyl, $C_3$-$C_6$ cycloalkyl, $C_1$-$C_6$ alkyl substituted with cyano or halogen, propagyl, allyl, or benzyl;
or a non-toxic salt thereof.

2. The 1,2,4-triazole derivative according to claim 1, which is selected from the group consisting of:
4-(3-mercapto-5-phenyl-1,2,4-triazole-1-yl)-benzenesulfonamide;
4-(3-hydroxy-5-phenyl-1,2,4-triazole-1-yl)-benzenesulfonamide;
4-[3-hydroxy-5-(4-methoxyphenyl)-1,2,4-triazole-1-yl]-benzenesulfonamide;
4-[3-hydroxy-5-(4-ethoxyphenyl)-1,2,4-triazole-1-yl]-benzenesulfonamide;
4-[3-hydroxy-5-(4-fluorophenyl)-1,2,4-triazole-1-yl]-benzenesulfonamide;
4-[3-hydroxy-5-(4-bromophenyl)-1,2,4-triazole-1-yl]-benzenesulfonamide;
4-[3-hydroxy-5-(3-fluoro-4-methoxyphenyl)-1,2,4-triazole-1-yl]-benzenesulfonamide;
1-(4-methanesulfonylphenyl)-5-phenyl-1H-1,2,4-triazole-3-ol;
1-(4-methanesulfonylphenyl)-5-(4-methoxyphenyl)-1H-1,2,4-triazole-3-ol;
4-(3-methoxy-5-phenyl-1,2,4-triazole-1-yl)-benzenesulfonamide;
4-[3-methoxy-5-(4-fluorophenyl)-1,2,4-triazole-1-yl]-benzenesulfonamide;
4-[3-methoxy-5-(4-methoxyphenyl)-1,2,4-triazole-1-yl]-benzenesulfonamide;
4-[3-methoxy-5-(4-bromophenyl)-1,2,4-triazole-1-yl]-benzenesulfonamide;
4-[3-methoxy-5-(3-fluoro-4-methoxyphenyl)-1,2,4-triazole-1-yl]-benzenesulfonamide;
4-(3-methylthio-5-phenyl-1,2,4-triazole-1-yl)-benzenesulfonamide;
4-(3-ethoxy-5-phenyl-1,2,4-triazole-1-yl)-benzenesulfonamide;
4-[3-ethoxy-5-(4-fluorophenyl)-1,2,4-triazole-1-yl]-benzenesulfonamide;
4-[3-ethoxy-5-(4-methoxyphenyl)-1,2,4-triazole-1-yl]-benzenesulfonamide;
4-[3-ethoxy-5-(3-fluoro-4-methoxyphenyl)-1,2,4-triazole-1-yl]-benzenesulfonamide;
4-(3-ethylthio-5-phenyl-1,2,4-triazole-1-yl)-benzenesulfonamide;
4-[3-propoxy-5-(4-methoxyphenyl)-1,2,4-triazole-1-yl]-benzenesulfonamide;
4-[3-propoxy-5-(4-fluorophenyl)-1,2,4-triazole-1-yl]-benzenesulfonamide;
4-[3-cyclopentyloxy-5-(4-fluorophenyl)-1,2,4-triazole-1-yl]-benzenesulfonamide;
4-[3-cyclopentyloxy-5-(4-methoxyphenyl)-1,2,4-triazole-1-yl]-benzenesulfonamide;
4-[3-cyclohexyloxy-5-(4-fluorophenyl)-1,2,4-triazole-1-yl]-benzenesulfonamide;
4-[3-cyclohexyloxy-5-(4-methoxyphenyl)-1,2,4-triazole-1-yl]-benzenesulfonamide;
4-(3-isopropoxy-5-phenyl-1,2,4-triazole-1-yl)-benzenesulfonamide;
4-[3-isopropoxy-5-(4-fluorophenyl)-1,2,4-triazole-1-yl]-benzenesulfonamide;
4-[3-isopropoxy-5-(–4-methoxyphenyl)-1,2,4-triazole-1-yl]-benzenesulfonamide;
4-(3-isopropylthio-5-phenyl-1,2,4-triazole-1-yl)-benzenesulfonamide;
4-(3-allyloxy-5-phenyl-1,2,4-triazole-1-yl)-benzenesulfonamide;
4-[3-allyloxy-5-(4-fluorophenyl)-1,2,4-triazole-1-yl]-benzenesulfonamide;
4-[3-allyloxy-5-(4-methoxyphenyl)-1,2,4-triazole-1-yl]-benzenesulfonamide;
4-[3-cyanomethoxy-5-(4-fluorophenyl)-1,2,4-triazole-1-yl]-benzenesulfonamide;
4-[3-cyanomethoxy-5-(4-methoxyphenyl)-1,2,4-triazole-1-yl]-benzenesulfonamide;
4-(3-benzyloxy-5-phenyl-1,2,4-triazole-1-yl)-benzenesulfonamide;
4-[3-benzyloxy-5-(3-fluoro-4-methoxyphenyl)-1,2,4-triazole-1-yl]-benzenesulfonamide;
4-[3-(2-chloroethoxy)-5-phenyl-1,2,4-triazole-1-yl]-benzenesulfonamide;
4-[3-(2,2,2-trifluoroethoxy)-5-(4-methoxyphenyl)-1,2,4-triazole-1-yl]-benzenesulfonamide;
4-[3-(2,2,-trifluoroethoxy)-5-(4-fluorophenyl)-1,2,4-triazole-1-yl]-benzenesulfonamide;
4-[3-cyclopropoxy-5-phenyl-1,2,4-triazole-1-yl]-benzenesulfonamide;
4-[3-prop-2-ynyloxy-5-(4-methoxyphenyl)-1,2,4-triazole-1-yl]-benzenesulfonamide;
4-[3-prop-2-ynyloxy-5-(4-fluorophenyl)-1,2,4-triazole-1-yl]-benzenesulfonamide;
4-(3-propy-2-nylthio-5-phenyl-1,2,4-triazole-1-yl)-benzenesulfonamide;
1-(4-methanesulfonylphenyl)-3-methoxy-5-phenyl-1H-1,2,4-triazole;
1-(4-methanesulfonylphenyl)-3-methoxy-5-(4-methoxyphenyl)-1H-1,2,4-triazole;
1-(4-methanesulfonylphenyl)-3-ethoxy-5-phenyl-1H-1,2,4-triazole;
1-(4-methanesulfonylphenyl)-3-ethoxy-5-(4-methoxyphenyl)-1H-1,2,4-triazole;
1-(4-methanesulfonylphenyl)-3-isopropoxy-5-phenyl-1H-1,2,4-triazole; and
1-(4-methanesulfonylphenyl)-3-isopropoxy-5-(4-methoxyphenyl)-1H-1,2,4-triazole;
or a non-toxic salt thereof.

3. A method for preparing a 1,2,4-triazole derivative of formula 1b

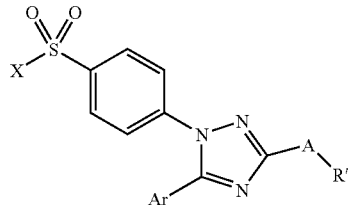

Formula 1b wherein:
X represents methyl or amino;
Ar represents phenyl or phenyl substituted with one or more radicals selected from the group consisting of $C_1$-$C_6$ alkoxy and halogen;
A represents O or S; and
R' represents $C_1$-$C_6$ alkyl, trifluoro $C_1$-$C_6$ alkyl, $C_3$-$C_6$ cycloalkyl, $C_1$-$C_6$ alkyl substituted with cyano or halogen, propagyl, allyl, or benzyl:

which comprises reacting a compound of formula 1a

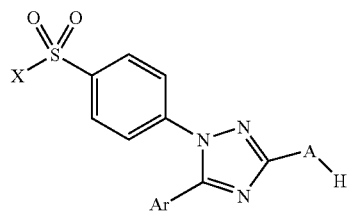

Formula 1a wherein:
X, Ar, and A are as defined in formula 1b
with R'—Br or R'—I in the presence of a at least one base selected from the group consisting of triethyl amine, trimethyl amine, tripropyl amine, pyridine, imidazole, sodium acetate, sodium hydroxide, sodium hydride, potassium hydroxide, sodium carbonate, and potassium carbonate, wherein R' is as defined in formula 1b.

* * * * *